United States Patent [19]

Konttinen et al.

[11] 4,097,338

[45] Jun. 27, 1978

[54] FLUORIMETRIC DEMONSTRATION AND DETERMINATION OF A REDUCED COENZYME OR DERIVATIVE IN AN AQUEOUS SYSTEM

[75] Inventors: Aarne Ilmari Konttinen, Helsinki, Finland; Bastiaan Cornelis Goverde; Peter Silvester Lambertus Janssen, both of Oss, Netherlands

[73] Assignee: Akzona Incorporated, Asheville, N.C.

[21] Appl. No.: 651,101

[22] Filed: Jan. 21, 1976

[30] Foreign Application Priority Data

Jan. 28, 1975 Netherlands .......................... 7500951

[51] Int. Cl.$^2$ ............................................. G01N 31/14
[52] U.S. Cl. .............................. 195/103.5 R; 23/230 B
[58] Field of Search ............ 195/103.5, 127, 103.5 R; 23/230 B

[56] References Cited

U.S. PATENT DOCUMENTS

| | | | |
|---|---|---|---|
| 3,384,555 | 5/1968 | Guilbault et al. .............. | 195/103.5 R |
| 3,637,655 | 1/1972 | Clendenning ................ | 195/103.5 R |
| 3,660,240 | 5/1972 | Chappelle et al. ............ | 195/103.5 R |
| 3,746,625 | 7/1973 | Bergmeyer et al. .......... | 195/103.5 R |
| 3,764,478 | 10/1973 | Bergmeyer et al. .......... | 195/103.5 R |

OTHER PUBLICATIONS

Lowry et al., J. Biol. Chem., vol. 224 (1957), pp. 1047–1064.

*Primary Examiner*—Alvin E. Tanenholtz
*Attorney, Agent, or Firm*—Robert H. Falk; Charles A. Wendel; Francis W. Young

[57] ABSTRACT

The present invention relates to a rapid and sensitive method for the determination of a reduced coenzyme, particularly NADH, NADPH and derivatives thereof, in that the fluorescence of such a reduced coenzyme in an aqueous medium is measured in the presence simultaneously of an organic liquid miscible with water and a dipersion of one or more slightly soluble or insoluble substances.

7 Claims, No Drawings

FLUORIMETRIC DEMONSTRATION AND DETERMINATION OF A REDUCED COENZYME OR DERIVATIVE IN AN AQUEOUS SYSTEM

The invention relates to a method for the demonstration and determination by fluorimetric means of a reduced coenzyme or a derivative thereof in an aqueous system.

A reduced coenzyme may be determined by spectrophotometric means or by fluorimetric means. A large number of enzymatic determinations are for example made by spectrophotometric methods and are then based on the measurement of one of the coenzymes participating in the reaction. In such cases use is usually made of the fact that the reduced form of the coenzyme shows an absorption maximum at a certain wave-length and that the oxidized form shows no absorption at this wavelength or in the region that includes this wavelength. The reduced forms of the coenzymes NAD and NADP, namely NADH and NADPH respectively, show for example absorption maxima at 345 nm, while the oxidized forms of these coenzymes show almost no absorption between 300 and 400 nm. The UV-spectrophotometric measurement here referred to is however not very sensitive.

In the spectrophotometric determination of reduced co-enzymes, use is also made of redox compounds, such as tetrazolium salts, in the presence of a suitable electron acceptor, such as, for example, phenazine methosulphate (PMS). In the presence of PMS, tetrazolium salts are converted by reduced coenzymes, such as, for example, NADH and NADPH, into coloured compounds, the so-called formazans. These methods, however, leave much to be desired because of their low sensitivity and lack of specificity, in particular when they are used for clinical purposes.

The fluorimetric determination offers a relatively more sensitive method for the demonstration and estimation of a reduced coenzyme. In absolute terms this method is still very insensitive because the native fluorescence of reduced coenzymes is in general slight.

A pre-requisite for a rapid, sensitive and reliable method is that the native fluorescence of a reduced coenzyme, even when this is present in low concentration, is unequivocally measurable and is not affected by other factors which may possibly be present in the aqueous system.

Surprisingly, such a method was met with in a method for the fluorimetric demonstration and determination of a reduced coenzyme, or a derivative thereof, in an aqueous system, characterized by the fact that the fluorescence is measured in the presence simultaneously of an organic liquid miscible with water or water-miscible mixture of organic liquids and a dispersion of one or more slightly soluble or insoluble substances of organic and/or inorganic nature, being formed in situ by means of precipitation and/or being added as such. The simultaneous presence of a dispersion of one or more difficultly soluble or insoluble substances and a water-miscible organic liquid or a water-miscible mixture of organic liquids appears surprisingly to intensify the native fluorescence of reduced coenzymes or their derivates considerably. An advantage directly resulting from this is that with the aid of the method according to the present invention, much lower concentrations of reduced coenzyme or derivatives thereof may now be demonstrated and estimated in a very simple manner than has until now been possible by fluorimetric methods. A further advantage is that in may cases smaller quantities of in general very expensive reagents may suffice. It is true that it is possible to intensify the native fluorescence of a reduced coenzyme or derivative by adding a water-miscible organic liquid, for example acetone, to the aqueous system containing the substance. In this way, however, the intensity of the native fluorescence can be slightly increased. The presence of a water-miscible organic liquid or mixture of liquids together with a dispersion of one or more difficulty soluble or insoluble substances of inorganic and/or organic nature, whether these are formed in situ by means of precipitation, and/or are added as such, appears however to intensify the native fluorescence many times. It has, for example, been found possible to intensify the native fluorescence of NADPH, which is normally not, or scarcely, measurable in water, about 60-fold by use of the method herein described. In general, the native fluorescence of a reduced coenzyme can be intensified by a factor of twenty to more than fifty with the aid of the present invention. A synergistic effect of such an order of magnitude was not to be expected and is therefore very surprising.

Although in principle any substance which is insoluble or only soluble with difficulty under the conditions of measurement can be used, use is preferably made of proteins precipitated in situ, being enzyme proteins or other proteins precipitated in situ, and inorganic compounds precipitated in situ or added as such, as well as combinations of two or more of these categories. An in situ formed, difficulty soluble or insoluble substance can be obtained by precipitating any protein possibly present in the aqueous system containing the reduced coenzyme or a derivative thereof. This protein may be enzyme protein or another protein. If the reduced coenzyme is demonstrated or estimated as a component of an enzyme reaction, then the precipitated protein will be derived completely or partly from the enzyme present. The intensification of the fluorescence appears to increase in proportion to the amount of precipitated enzyme present until an optimal value has been reached. The presence of a relatively high amount of precipitated protein occurs if the reduced coenzyme is a component of a reaction mixture of different, possibly interacting, enzyme reactions, or if an enzyme reaction takes place in an aqueous system that already contains protein for some other reason, such as, for example, blood serum. It is therefore preferable that a protein for precipitation be added to an aqueous system which does not contain protein or contains only enzyme protein. In principle, any protein or polypeptide can be used for the addition, for example, a protein of animal or plant origin. Good results are obtained after the addition of, for example, albumin.

After precipitation of the already present and/or added protein, the fluorescence is demonstrated or measured in the thus-obtained heterogenous system in the presence of a water-miscible organic liquid or a water-miscible mixture of organic liquids.

This organic liquid or a combination of such liquids can at the same time function as a protein-precipitating reagent, but it is also possible to precipitate the protein with the aid of other suitable agents. When other precipitating agents are used, a water-miscible organic liquid or a combination of such still has to be added to the aqueous test system as well.

Other substances which are insoluble or soluble only with difficulty under the test conditions may be used in addition to, or instead of, precipitated protein in the method according to the present invention. Such substances may be of organic or inorganic nature.

Use is preferably made of substances belonging to the last-named category, such as inorganic salts which are insoluble or soluble only with difficulty in the test medium.

These can be obtained in a known way, for example by adding to the aqueous system two salts soluble in water, whereby the metal ion of the one salt provides the insoluble or difficulty soluble substance with the anion of the other salt. Divalent or multivalent metal ions are preferably used as the metal ion.

In cases where the present method is applied to an aqueous system containing a reaction mixture of an enzyme reaction, the metal ion of the relevant enzyme activator can be utilized. In that case, only a compound possessing a precipitating anion need be added. When the concentration of this metal ion is very low, more of the same metal ion, or another suitable metal ion, may be added is desired. It is obvious that whenever a suitable anion is already present, it may suffice to add a suitable metal compound. Suitable metal compounds are for example water-soluble inorganic salts of metals such as zinc, magnesium, manganese, calcium and aluminium. Suitable anions include $HCO_3^-$, $HPO_4^{2-}$ and $SO_4^{2-}$, or those derived from oxalic acid, citric acid and tartaric acid.

The difficultly soluble or insoluble substance can also be added to the liquid to be tested as such. In this case, use is preferably made of inorganic substances, such as, for example, metal carbonates, metal sulphates, metal phosphates, metal silicates and metal oxides which are insoluble or soluble only with difficulty under the test conditions. Examples of such substances include zinc carbonate, magnesium carbonate, calcium phosphate, zinc phosphate, calcium sulphate (gypsum powder), aluminium oxide, silica and powdered natural silicates. The preferred final concentration of the difficultly soluble or insoluble inorganic compound is between 10 and 250 mmol/liter.

The choice of such a compound will in general depend on the pH of the liquid containing the reduced coenzyme to be determined, or, more generally, on the pH or range of pH values at or over which the reduced coenzyme is stable. In most cases measurements will be made in a neutral or weak alkaline medium.

The use of difficultly soluble or insoluble inorganic compounds instead of a protein precipitate in estimations performed with, for example, sera with variable protein concentrations has the advantage that there can no longer be any question of dependence on the protein concentration, which is certainly the case if protein precipitation is used. After all, as is made obvious above, the protein concentration has considerable influence on the fluorescence.

The present method can in principle be applied to any aqueous system containing a reduced coenzyme. The simplest example of this is a solution of NADH in water. The method can, however, also be used successfully with more complex aqueous systems, such as biological fluids. The concept of a biological fluid includes: blood, plasma, serum, cerebrospinal fluid, cervical fluid, saliva, bile, synovial fluid, urine and also fluids of microbiological origin, such as culture media. As already stated above, in general no additional protein needs to be added to a biological fluid as a starting material for the formation of a precipitate.

The method can be used successfully for the demonstration and estimation of a reduced coenzyme which is the reaction product of an enzyme reaction, for example, summarily represented as:

$$CH_3COCOOH + HS\text{-}CoA + NAD \rightleftharpoons CH_3CO\text{-}S\text{-}CoA + CO_2 + NADH + H^+$$

in which HS-CoA represents coenzyme A, NAD coenzyme I and NADH the reduced form of coenzyme I.

Good results are also obtained when the method is used with reaction mixtures of enzyme reactions, in which a dehydrogenase, a substrate for the dehydrogenase and the oxidized form of a coenzyme are the reaction products. Examples of such reactions include the following:

Isocitric acid + NADP (coenzyme II) 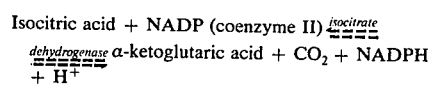 α-ketoglutaric acid + $CO_2$ + NADPH + $H^+$ Malic acid + NAD (coenzyme I) 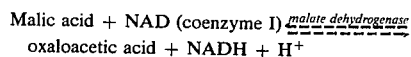 oxaloacetic acid + NADH + $H^+$ Glucose-6-phosphate + NADP glucose-6-phosphate dehydrogenase 6-phosphogluconate + NADPH + $H^+$ The reaction system chosen does not however have to be restricted to an enzyme reaction involving a dehydrogenase with the simultaneous formation of a reduced coenzyme. The enzyme reaction in which this happens may also be preceded by one or more other reactions, which may be enzymatic or non-enzymatic. For example, the last reaction given above, with glucose-6-phosphate dehydrogenase (G-6-PD) is the reaction step in which the reduced coenzyme NADPH is formed and which may therefore be called the indicator reaction, and it can be preceded by, for example, the following reaction:

glucose + adenosine triphosphate (ATP) 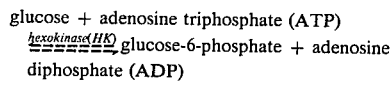 glucose-6-phosphate + adenosine diphosphate (ADP)

and this reaction step can again be preceded by the reaction:

creatine phosphate (CP) + ADP 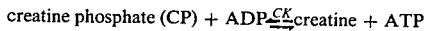 creatine + ATP

CK = creatine kinase.

The quantity of reduced coenzyme is a measure of the quantity of the component to be determined in the indicator reaction. In case the indicator reaction is preceded by one or more other reaction the determined quantity of reduced coenzyme is a measure of the quantity of the component to be determined in these preceding reactions provided that optimal reaction conditions have been chosen. If the component to be determined is an enzyme the determined quantity of reduced coenzyme in the indicator reaction can also be a measure of the activity of the enzyme in question.

The method herein referred to therefore offers, as one of its possibilities, a rapid and good possibility for the determination of creatine kinase. Since creatine kinase (CK) is found as a muscle-specific enzyme in certain body fluids during pathological processes, this means that the present method also offers a rapid and reliable possibility for the demonstration of myocardial infarction and other conditions, and it also indicates the extent of the manifestation which has appeared.

In the above examples the reduced coenzyme formed is always demonstrated or estimated quantitatively. If the reactions go in the opposite direction, however, it is also possible to demonstrate a decrease in the amount of reduced coenzyme or to determine this quantitatively. In other words, it is also possible to measure the decrease in the fluorescence. Prerequisites for this are however that the fluorescence in the initial phase is strong enough and that the fluorescence in the final phase can still be sufficiently intensified to be readily measurable. Use of the present invention enables these conditions to be readily complied with. In this case, in which the reduced coenzyme is thus the starting product, the fluorescence has to be measured both in the initial phase and the final phase. For the determination of the fluorescence in the initial phase, a measured aliquot of the liquid under test is taken and subjected to the present method separately.

In this case, the decrease in fluorescence, or better the quantity of reduced coenzyme still present, is a measure for the reaction component to be determined. If the indicator reaction, consequently the reaction in which the reduced coenzyme is oxidized, is preceded by one or more other reactions, enzymatic or non-enzymatic, then the quantity of reduced coenzyme (still) present is a measure of the quantity of the component to be determined in the system.

This variant lends itself very well for another type of estimation, such as is given below, by way of example, for the determination of creatine kinase:

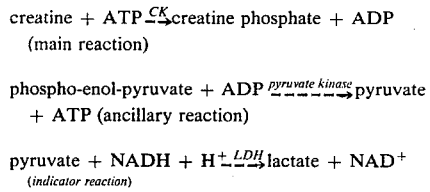

creatine + ATP $\overset{CK}{\rightleftharpoons}$ creatine phosphate + ADP
(main reaction)

phospho-enol-pyruvate + ADP $\overset{pyruvate\ kinase}{\longrightarrow}$ pyruvate + ATP (ancillary reaction)

pyruvate + NADH + H$^+$ $\overset{LDH}{\rightleftharpoons}$ lactate + NAD$^+$
(indicator reaction)

where LDH stands for lactate dehydrogenase.

From the above example it is obvious that a distinction may be made between main reaction, ancillary reaction and indicator reaction. By indicator reactions is meant the reaction in which the reduced coenzyme is formed or is oxidized. If in the last example the main reaction is omitted, the ancillary reaction has become the main reaction. Although the present invention is in principle applicable to every reduced coenzyme, the reduced pyridine nucleotides and derivatives thereof, in particular NADH and NADPH and derivatives, are preferred. By derivatives are meant here, for example, the acyl compounds, such as the acetylpyridine compounds.

As water-miscible organic liquids, the following may be used: methanol, ethanol, 2-propanol, ethylene glycol, propylene glycol, 2-methoxy-ethanol (methyl cellosolve), 2-ethoxyethanol (ethylcellosolve), 2-(ethoxyethoxy)ethanol, glycerol, acetone, methyl-ethyl-ketone, dimethyl sulfoxide (DMSO), formamide, dimethyl formamide (DMF), pyridine and such, or a mixture of two or more of these.

Most of these liquids and their mixtures are in addition also suitable as protein-precipitating agents or constituents thereof. For precipitation of protein a mixture composed of acetone, methanol, ethanol and 2-methoxyethanol can be used. Good results are obtained using a mixture of the following composition:

| | |
|---|---|
| acetone | 20 parts by volume |
| methanol | 10 parts by volume |
| ethanol | 30 parts by volume |
| ethyleneglycol monoethylether | 20 parts by volume |

If the difficultly soluble or insoluble substance comprises only an inorganic salt, very good results can also be obtained if as the water-miscible organic liquid an organic liquid is used which does not belong to the series of the conventional protein-precipitating organic solvents.

A preferred method according to the invention is the addition of a suspension of solid particles in an organic liquid, the latter preferably having no protein precipitating properties. As an example of such a preferred method is the use of a suspension of an insoluble zinc salts in ethyleneglycol. The zinc salt may be the reaction product of zinc sulphate and sodium bicarbonate.

The invention also relates to diagnostic test-kits to be used by the method according to the invention. Such test-kits then contain, in addition to buffered enzyme-substrate mixtures, coenzymes, stabilizers, metal activators and SH-protecting agents, as necessary a protein and/or one di - or multivalent metal salt soluble in water and/or a salt of which the anion gives a difficultly soluble or insoluble inorganic precipitate or a salt which is as much insoluble or soluble only with difficulty, such as described above, and a water-miscible organic solvent or a water-miscible mixture of organic solvents, as described above. The invention relates therefore to diagnostic test-kits with the above-noted contents.

If the estimation takes place in a system in which one or more enzyme reactions plays or play a decisive role, then the aqueous system has to be incubated for a certain period of time. The duration of the incubation depends amongst others on the temperature chosen and at 25° C will generally be longer than at an incubation temperature of 37° C. The incubation is performed in the way usual for such systems.

The fluorimetric estimation may be performed in a very simple manner with the aid of a fluorimeter. If use is made of a few standard solutions for reference purposes, a system provided with a simple U.V. lamp may even suffice.

| Abbreviations used | |
|---|---|
| NAD | nicotinamide-adenine-dinucleotide |
| NADH | reduced NAD |
| NADA | nicotinamide-adenine-dinucleotide phosphate |
| NADPH | reduced NADP |
| APAD | acetylpyridine-adenine-dinucleotide |
| APADH | reduced APAD |
| AMP | adenosine-5'-monophosphate |
| ADP | adenosine-5'-diphosphate |
| ATP | adenosine-5'-triphosphate |
| PEP | phospho-enolpyruvate |
| GSH | glutathione |
| G-6-PDH | glucose-6-phosphate dehydrogenase |
| HK | hexokinase |
| SDH | sorbitol dehydrogenase |
| CK | creatine kinase |

EXAMPLE I

The following reagents are consecutively pipetted into two measuring cuvettes labelled A and B: 0.25 ml 10$^{-5}$M NADH in 0.05 M tris (hydroxymethyl) aminomethane buffer, pH 7.5; 0.25 ml of a 4% solution of bovine serum albumin in the same buffer.

3.75 ml physiological saline is added to cuvette A and 3.75 ml 2-methoxyethanol is added to cuvette B.

After homogenization of the contents of both cuvettes, the fluorescence is determined under the optimal conditions of excitation and emission.

In cuvette B, the intensity of the fluorescence measured is 50 times as great as in cuvette A, which contains neither precipitated protein nor 2-methoxyethanol.

EXAMPLE II 0.5 ml aliquots of a $10^{-4}$ M solution of NADPH in 0.1 M triethanolamine buffer, pH 7.0, are pipetted into two measuring cuvettes labelled A and B.

0.5 ml distilled water is then added to cuvette A, and 0.25 ml 0.5 M zinc sulphate solution followed by 0.25 0.5 M sodium bicarbonate solution is added to cuvette B.

After vigorous shaking of the gelatinous suspension in cuvette B, 3.75 ml ethyleneglycol is added to both cuvettes.

The intensity of the fluorescence in cuvette B appears to be 12 times as great as that in cuvette A, which contains ethyleneglycol but no zinc salt.

EXAMPLE III 0.5 ml $10^{-6}$ M APADH is added to a gelatinous heterogenous system, made by mixing 0.25 ml 0.5 M magnesium chloride solution and 0.25 ml 0.5 M sodium hydrogen phosphate solution. After vigorous shaking, 4.5 ml of a 10% solution of glycerol in ethanol is added. The intensity of the fluorescence is intensified by a factor of 66 compared with an identical system lacking the solid and the organic liquid.

EXAMPLE IV 0.25 ml of 0.05 m triethanolamine buffer (pH 7.6), in which 0.4 mM NADP and 40 mM magnesium acetate was dissolved, and 0.25 ml 14 mM glucose-6-phosphate in 0.05 M triethanolamine buffer (pH 7.6) are mixed in a tube, which is then placed in a waterbath at 37° C for 5 minutes. Subsequently 25 $\mu$l of a haemolysate of human erythrocytes is pipetted into the tube, after which the liquid is incubated at 37° C for 15 minutes. Finally 3.75 ml of a 1% suspension of finely-divided calcium sulphate in ethylene glycol is added. The fluorescence-activity ($\lambda$exc. = 345 nm; $\lambda$em = 435 nm) is 12 times as great as that of an identical system lacking the calcium sulphate and about 30 times as great as an identical system containing neither calcium sulphate nor ethylene glycol.

The method can therefore be used as a sensitive method for the determination of the glucose-6-phosphate dehydrogenase activity in erythrocytes.

EXAMPLE V 0.5 ml of a solution of magnesium acetate (2mMol), ATP (0.2 mMol), NADP (0.2mMol), bovine serum albumin (230 mg), HK from yeast (25 units) and G-6-PDH (35 units) in 100 ml 0.25 M tris(hydroxymethyl) aminomethane buffer (pH 7.5) is briefly warmed to 37° C. Subsequently, 10 $\mu$l of blood serum is added, after which the mixture is incubated at 37° C for 10 minutes.

3.9 ml of a mixture of analytically pure acetone, ethanol and 2-methoxyethanol in the ratios (v/v) 20:30:50 is then added and the whole is shaken. The fluorescence is measured under the same conditions as in Example IV.

The intensity of the fluorescence is 54 times as great as that of an identical incubation mixture containing a physiological saline solution instead of a mixture of organic liquids.

EXAMPLE VI

200 $\mu$l of a solution of 0.1 mM NADH in 0.1M triethanolamine buffer (pH 7.4) and 20 $\mu$l of serum are mixed in two measuring cuvettes labelled A and B. The cuvettes are subsequently placed in a waterbath at 25° C for 30 minutes, after which 200 $\mu$l aliquots of a 100 mM solution of fructose in the above-mentioned buffer are added (time 0).

After exactly 5 minutes incubation at 25° C, 3.0 ml dimethylformamide is added to cuvette A, and after exactly 10 minutes incubation the same quantity of dimethylformamide is added to cuvette B. 200 $\mu$l NADH solution, 200 $\mu$l fructose solution, 3.0 ml dimethylformamide and 20 $\mu$l serum, as specified above, are then added consecutively to a cuvette marked C, after which the intensity of fluorescence in the three cuvettes is measured under optimal conditions. The sorbitol dehydrogenase activity of the serum can be determined very sensitively from the differences in the intensities of fluorescence between cuvettes A and B with reference to cuvette C, while the consumption of expensive reagents is only 5% with respect to that of the conventional UV and fluorimetric techniques.

EXAMPLE VII

A lyophilized enzyme-substrate mixture, which contains per vial:

300 $\mu$g creatine phosphate
35 $\mu$g ADP
400 $\mu$g AMP
35 $\mu$g NADP
250 $\mu$g glucose
1 mg magnesium acetate
200 $\mu$g glutathione
200 $\mu$g dithiothreitol
0.02 units hexokinase
0.01 units glucose-6-phosphate dehydrogenase is dissolved in 200 $\mu$l 0.05 tris (hydroxymethyl)-aminomethane buffer at pH 7.4. 10 $\mu$l plasma is then added and the mixture obtained is incubated at 37° C for 15 minutes.

Finally a mixture consisting of equal parts of acetone, methanol, ethanol and 2-methoxyethanol is added. After shaking, the intensity of the fluorescence is measured at an excitatory wave-length of 345 nm and at an emission wave-length of 435 nm, and compared with that of an aqueous solution of quininesulphate (1 $\mu$g/ml). Using this procedure the creatine kinase activity of patient's blood can be estimated rapidly and simply, while the estimation can be performed with 1% of the quantity of reagents necessary for estimations using conventional UV and fluorimetric techniques.

In another test 200 $\mu$l of the above buffered enzyme solution has been mixed with 1.5 ml of a mixture consisting of:

70 ml 0.5 M ZnSO$_4$-solution
70 ml 0.5 M NaHCO$_3$-solution
ethyleneglycol ad 1000 ml.

The intensity of the fluorescence was measured at an excitary wave-length of 345 nm and at an emission wave-length of 435 nm.

EXAMPLE VIII

A lyophilized mixture which contains per vial:
sodium pyruvate: 20 μg
β-NADH di-sodium salt: 40 μg
is dissolved in 300 μl 0.05 M phosphate buffer at pH 7.5. Subsequently 10 μl plasma is added and the mixture is incubated at 25° C for 5 minutes.

Finally 1.5 ml of a mixture consisting of:
30 ml CaCl$_2$: 2 M-solution
30 ml Na$_2$HPO$_4$: 2 M-solution
ethyleneglycol ad 1000 ml
is added, whereafter the intensity of the fluorescence is measured as described in the foregoing examples. Using this procedure the lactic dehydrogenase activity (LDH:EC 1.1.1.27) can be estimated in a very rapid and sensitive manner.

EXAMPLE IX a. Preparation of HCG-G6PDH conjugate.

10 mg human choriongonadotrophine (HCG) and 20 mg glucose-6 phosphate dehydrogenase (G 6 PDH) were dissolved in 2 ml 0.1 M phosphate buffer of pH 7.2 containing 0.25% (w/v) glutaric aldehyde. The mixture was shaken for 2 hours at room temperature and thereafter fractionated over Sephadex G-200 in 0.1 M phosphate buffer of pH 7.2. The fractions leaving the column without delay were collected (12 ml). These fractions contain both HCG (immunologically measured) and G 6 PDH (enzymatically measured).

b. Determination of the required quantity of HCG-G6PDH conjugate.

A dilution series was made of the collected fraction as described sub a. in 0.05 M triethanol amine buffer of pH 7.6 containing 0.1% (w/v) bovine serum albumin. The dilutions were from 1:10$^2$ to 1:10$^{10}$. After a preincubation at 37° C during 5 minutes 200 μl of each of the dilution series was added to a vial containing a preincubated mixture of 0.25 ml of a solution of 0.4 mM NADP and 40 mM Mg-acetate in 0.05 M triethanol amine buffer of pH 7.6, and 0.25 ml of a solution of 14 mM glucose-6-phosphate in 0.05 M triethanol amine buffer of pH 7.6.

The mixture was incubated at 37° C during 15 minutes whereafter 3.75 ml of a 1% suspension of finely-divided calcium sulphate in ethylene glycol was added. Finally the fluorescence activity was measured ($\lambda_{exc.}$ = 345 nm; $\lambda_{em}$ = 435 nm). Using this technique an enzyme activity could be measured in a dilution of 1:3×10$^4$.

We claim:

1. A method for the determination of a reduced co-enzyme selected from the group consisting of NADH and NADPH in an aqueous system by fluorometric means, comprising the steps of
preparing an aqueous sample containing said reduced co-enzyme wherein said aqueous sample contains as fluorescence intensifiers therefor (a) a water-miscible organic liquid or a mixture of such liquids, and (b) a dispersion of a water-insoluble material added thereto, said water-insoluble material selected from the group consisting of a metal carbonate, a metal sulphate, a metal phosphate, a metal silicate, a metal oxide, and a protein material obtained by precipitation of a protein in situ by the addition of another protein or a polypeptide to said aqueous sample for the precipitation of said water-insoluble material where no protein, or only enzyme protein, is present, and
measuring specifically the fluorescence of said reduced co-enzyme in said sample.

2. Method according to claim 1, in which said reduced co-enzyme is the reaction product of an enzymatic reaction and in which said water-miscible organic liquid is selected from the group consisting of methanol, ethanol, 2-propanol, ethylene glycol, propylene glycol, 2-methoxyethanol, 2-ethoxyethanol, 2(ethoxyethoxy)ethanol, glycerol, acetone, methyl-ethyl-ketone, dimethyl sulfoxide, formamide, dimethylformamide and pyridine, and a mixture of two or more thereof.

3. Method according to claim 2 in which said enzymatic reaction is preceded by at least one enzymatic or non-enzymatic reaction and in which the fluorimetrically determined quantity of reduced co-enzyme is a measure of the amount of reaction component to be determined in one of said participating reactions.

4. Method according to claim 2 in which said enzymatic reaction is preceded by a first reaction relating to creatine (phospho) kinase, a second reaction which is the ancillary reaction relating to a hexokinase, and in which the third reaction which is the indicator reaction in which the reduced co-enzyme is formed relating to glucose-6-phosphate dehydrogenase.

5. Method according to claim 2 in which said enzymatic reaction is preceded by a first reaction relating to creatine (phospho) kinase, the ancillary reaction relates to pyruvate kinase, and the indicator reaction in which the amount of reduced co-enzyme present decreases, relates to lactate dehydrogenase.

6. Method according to claim 1 in which said aqueous sample contains, as said fluorescence intensifiers, a suspension of an insoluble zinc salt in ethylene glycol.

7. Method according to claim 1 in which said water-insoluble material is selected from the group consisting of zinc carbonate, magnesium carbonate, calcium phosphate, zinc phosphate, calcuim sulphate, aluminum oxide, silica and powdered natural silicates.

* * * * *